United States Patent
Fini et al.

[11] Patent Number: 5,817,278
[45] Date of Patent: Oct. 6, 1998

[54] BLOOD OXYGENATOR AND METHOD OF OXYGENATING BLOOD

[75] Inventors: Massimo Fini, Mirandola; Nicola Ghelli, S. Pietro In Casale, both of Italy

[73] Assignee: Dideco S.P.A., Mirandola, Italy

[21] Appl. No.: 560,625

[22] Filed: Nov. 20, 1995

[30] Foreign Application Priority Data

Nov. 25, 1994 [IT] Italy .................. MI94A2403

[51] Int. Cl.$^6$ .......................... B01D 61/00; B01D 63/02; A61M 1/14; A61M 1/18
[52] U.S. Cl. ............... 422/45; 210/321.78; 210/321.79; 210/321.8; 210/321.81; 210/321.87; 210/321.88; 210/321.89; 210/321.9; 210/500.23; 424/44; 424/48
[58] Field of Search ................. 210/321.78, 321.79, 210/321.8, 321.81, 321.87, 321.89, 321.9, 500.23, 645; 422/44, 45, 46, 48

[56] References Cited

U.S. PATENT DOCUMENTS

| | | |
|---|---|---|
| 3,422,008 | 1/1969 | McLain . |
| 3,794,468 | 2/1974 | Leonard . |
| 4,572,446 | 2/1986 | Leonard et al. . |
| 4,622,206 | 11/1986 | Torgeson .................................. 422/48 |
| 4,639,353 | 1/1987 | Takemura et al. ........................ 422/46 |
| 4,690,758 | 9/1987 | Leonard et al. ........................ 210/247 |
| 4,715,953 | 12/1987 | Leonard ................ 210/321.8 |
| 4,722,829 | 2/1988 | Giter ........................................ 422/46 |
| 4,735,775 | 4/1988 | Leonard et al. .......................... 422/46 |
| 4,749,551 | 6/1988 | Borgione .................................. 422/48 |
| 4,770,852 | 9/1988 | Takahara et al. ........................ 422/48 |
| 4,808,378 | 2/1989 | Nakanishi et al. ...................... 422/48 |
| 4,876,066 | 10/1989 | Bringham et al. ....................... 422/46 |
| 4,940,617 | 7/1990 | Bearmeister ............................. 428/284 |
| 4,975,247 | 12/1990 | Badolato et al. ......................... 422/48 |
| 5,039,482 | 8/1991 | Panzani et al. ............................ 422/46 |
| 5,139,741 | 8/1992 | Hagiwara ................................. 422/48 |
| 5,152,964 | 10/1992 | Leonard ................................... 422/48 |
| 5,188,801 | 2/1993 | Fini ........................................... 422/48 |
| 5,236,586 | 8/1993 | Antoni et al. ........................ 210/321.8 |
| 5,236,665 | 8/1993 | Mathewson .............................. 422/46 |
| 5,240,677 | 8/1993 | Jones et al. .............................. 422/46 |
| 5,263,924 | 11/1993 | Mathewson .............................. 422/44 |
| 5,266,265 | 11/1993 | Raible ...................................... 422/46 |
| 5,316,724 | 5/1994 | Mathewson et al. .................... 422/48 |
| 5,376,334 | 12/1994 | Haworth et al. ......................... 422/46 |

*Primary Examiner*—John Kim
*Attorney, Agent, or Firm*—Popovich & Wiles P.A.

[57] ABSTRACT

A blood oxygenator having a substantially cylindrical structure provided with an inner wall or core and an outer wall that define an oxygenation chamber. The oxygenation chamber contains a hollow fiber bundle comprised of hollow microporous semi-permeable fibers which are meant to be affected externally by the blood that flows in the oxygenation chamber. The oxygenation chamber is provided with inlet and outlet paths for connection to the outside. The hollow fibers are embedded, at their ends, in rings of polyurethane resin known as potting and are connected to gas inlet and outlet chambers respectively for the intake of oxygen and for the discharge of the carbon dioxide. The structure includes ribs that extend from the inner wall of the structure and are divided into multiple sets that run longitudinally along the entire length of the core generally parallel with the axis of the core. The ribs are suitable to produce an arrangement in the fiber bundle so that the fiber bundle touches the outer wall of the structure in the regions where it touches the ribs and so that the fiber bundle is spaced from the outer wall and touches the inner wall of the structure in the regions between adjacent sets of ribs.

48 Claims, 7 Drawing Sheets

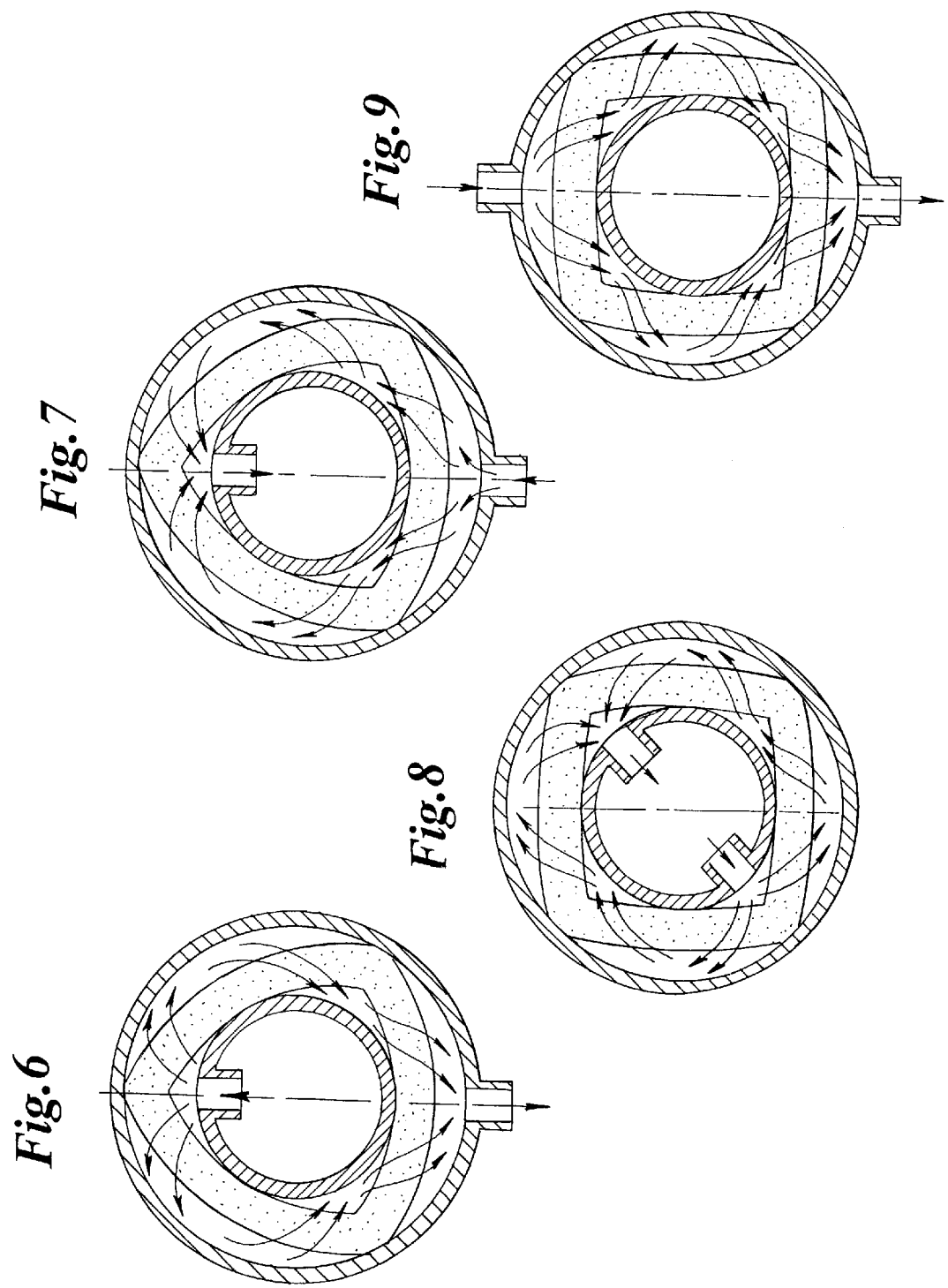

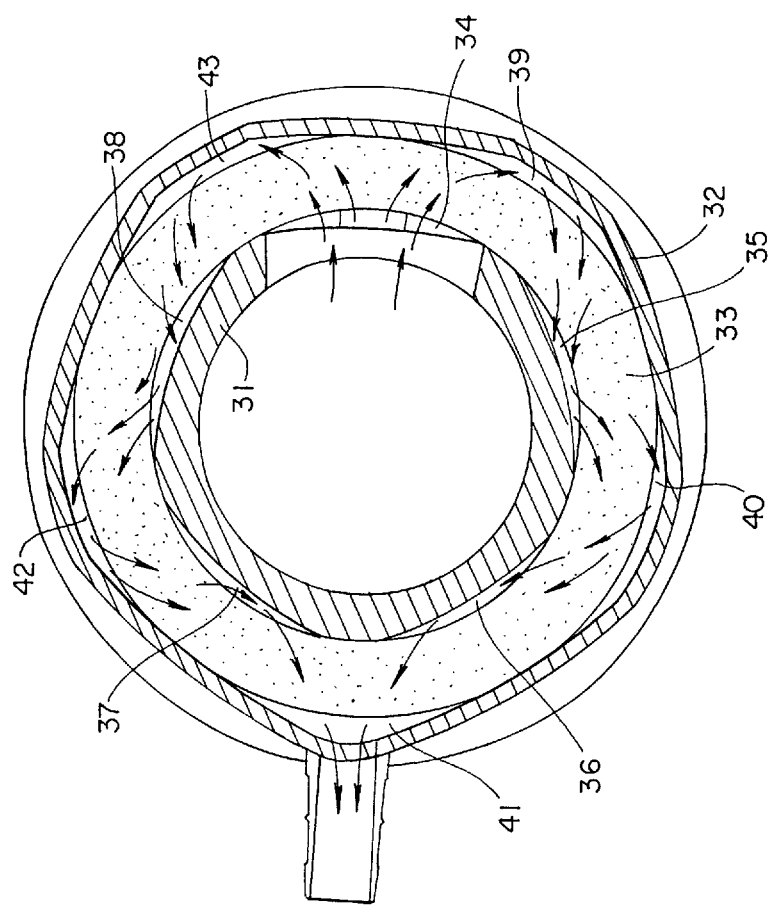

BLOOD OXYGENATOR AND METHOD OF OXYGENATING BLOOD

FIELD OF THE INVENTION

The present invention relates to a blood oxygenator. More particularly, the invention relates to oxygenating devices with a hollow fiber bundle between the inner wall of a core and an outer wall and having inner wall chambers and outer wall chambers located between the bundle and the inner wall and outer wall, respectively. The invention includes a method of oxygenating blood using the devices.

BACKGROUND OF THE INVENTION

It is known that extracorporeal circuits through which blood flows during surgery include an oxygenation device which has the purpose of transferring oxygen to the blood while removing carbon dioxide. The oxygenation devices proposed by the known art have many embodiments. However, all have some drawbacks.

Among the many types of oxygenators is an oxygenator in which a cylindrical structure comprises an inner wall or core and an outer wall. Both are smooth and suitable to define an annular oxygenation chamber that contains a hollow fiber bundle which is in contact with the walls over their entire extension. The hollow fiber bundle is comprised of layers of microporous hollow fiber membranes, which are meant to be affected externally by the blood that flows through the oxygenation chamber. The hollow fibers are embedded at their ends in rings of polyurethane resin, known as potting, and are open into chambers respectively for the intake of oxygen, which thus passes inside them, and for the discharge of the carbon dioxide removed from the blood.

In this type of known oxygenator the blood encounters considerable resistance in passing through the oxygenation chamber from the inlet to the outlet. The consequent heavy load losses produce a blood treatment that can cause hemolytic damage.

The aim of the present invention is to provide a blood oxygenator in which blood flow occurs with minimal load losses which allows operation with negligible risk of hemolytic damage.

SUMMARY OF THE INVENTION

The proposed aim is achieved by a blood oxygenator according to the invention, which comprises a substantially cylindrical structure having an inner wall or core and an outer wall which define the inner and outer bounds of an oxygenation chamber. The oxygenation chamber contains a fiber bundle comprised of hollow microporous semi-permeable membrane fibers which are meant to be affected externally by the blood that flows in the oxygenation chamber. The oxygenation chamber includes a blood inlet and a blood outlet positioned to cause blood to flow in a generally circumferential path through the fiber bundle. The hollow fibers are embedded, at each of their ends, in rings of polyurethane resin known as potting which seals the area between the fibers at each end. The seals at each end of the fibers together with the inner and outer walls define the oxygenation chamber. The lumens of the hollow fibers are connected to inlet and outlet chambers respectively for the intake of oxygen and for the discharge of carbon dioxide. The inner wall includes ribs that extend radially outward. The ribs are divided into multiple sets that run longitudinally along the entire length of the structure in a configuration that is generally parallel to the axis of the core. The rib sets space the fiber bundle from the inner wall to produce a plurality of longitudinal inner wall chambers. The fiber bundle touches the outer wall of the structure in the regions radially opposite the inner wall chambers (i.e. where the fiber bundle is spaced from the inner wall by the rib sets). The fiber bundle is spaced from the outer wall to form a plurality of outer wall chambers and touches the inner wall of the structure in the regions between two adjacent sets of ribs.

In one embodiment the core of the oxygenator is substantially cylindrical. The rib sets protrude into the oxygenation chamber and cause the fiber bundle to assume an undulated configuration. In another embodiment it is the core that has an undulated configuration. In that embodiment the ribs are positioned and configured in the troughs of the undulations which are substantially parallel to the axis of the core such that the fiber bundle assumes a substantially cylindrical configuration.

BRIEF DESCRIPTION OF THE DRAWINGS

Further characteristics and advantages will become apparent from the description of several preferred but not exclusive embodiments of the invention, illustrated only by way of non-limiting example in the accompanying drawings, wherein:

FIGS. 6–9 are schematic views of further embodiments of the invention.

FIG. 10 is another sectional view, similar to FIG. 2, of a further embodiment of the invention.

DETAILED DESCRIPTION OF THE INVENTION

Figure 1:
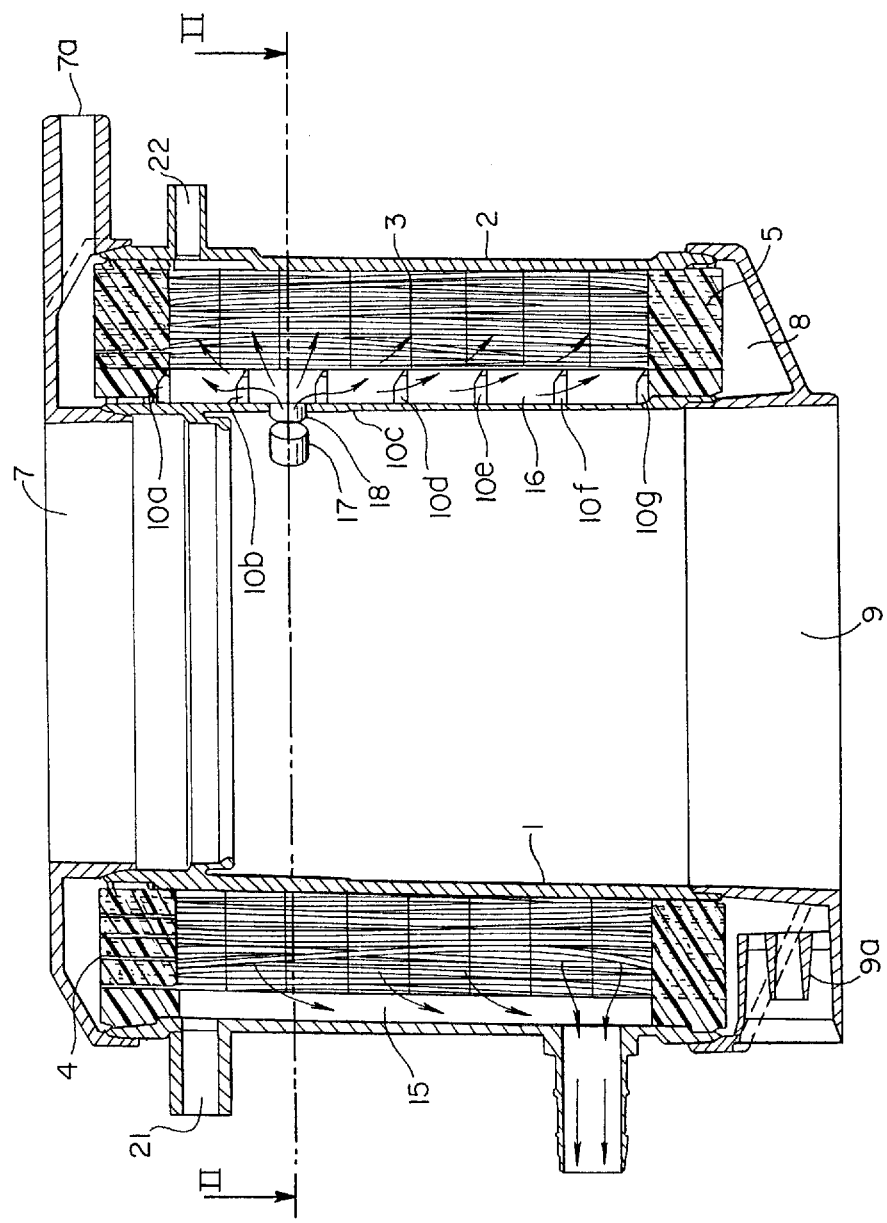
FIG. 1 is a sectional view, taken along the plane I-I of FIG. 2.
Figure 2:
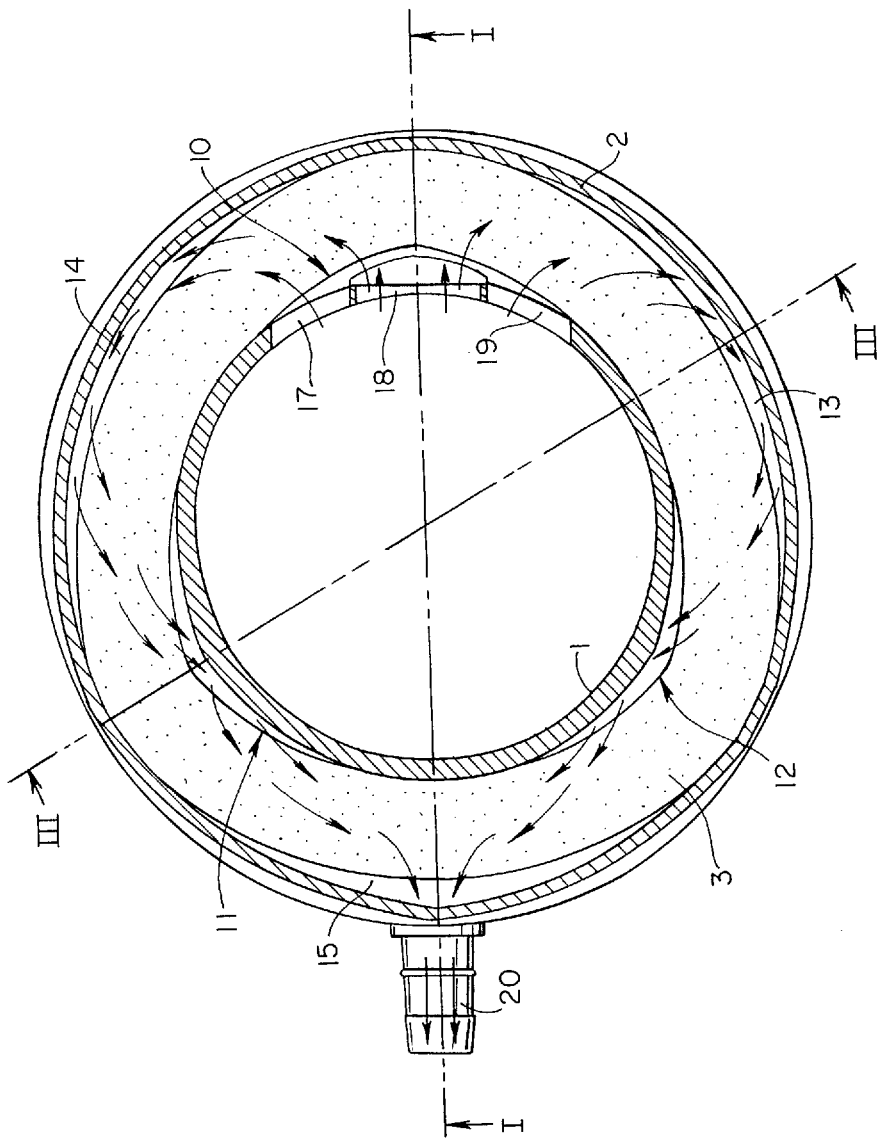
FIG. 2 is a sectional view, taken along the plane II-II of FIG. 1.
Figure 3:
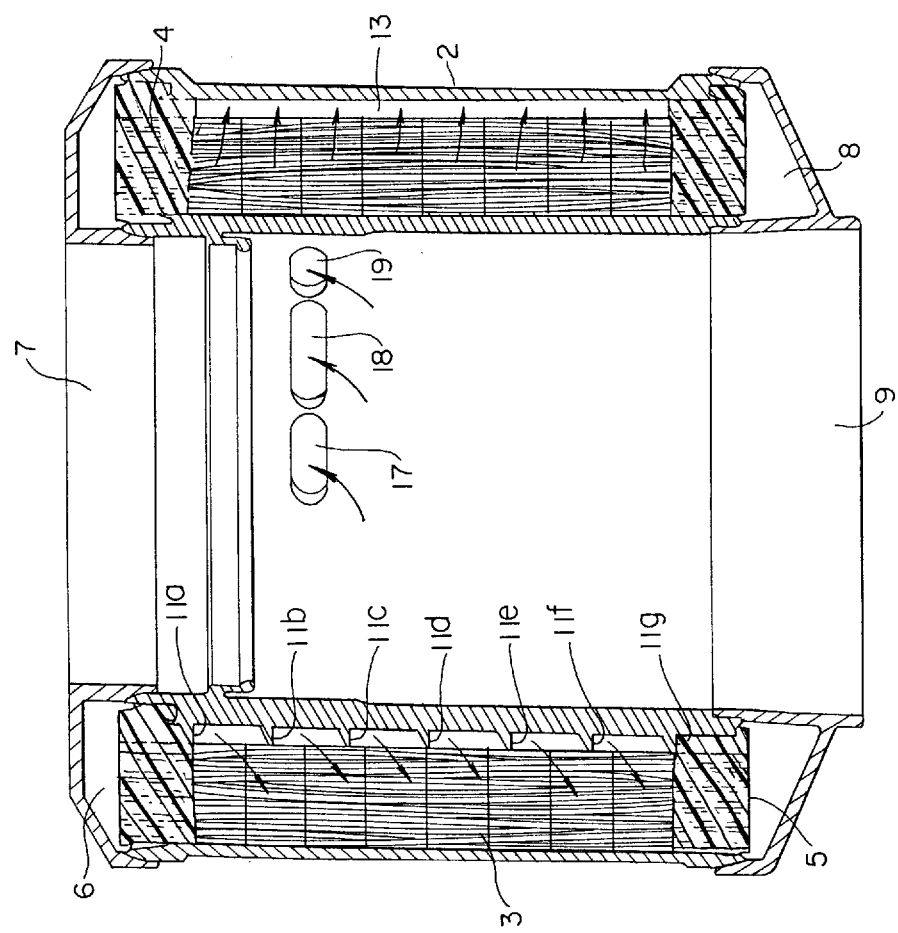
FIG. 3 is a sectional view, taken along the plane III-III of FIG. 2.

With respect to the above FIGS. 1, 2, and 3, the inner wall or core and the outer wall of the substantially cylindrical structure are designated by the referenced numerals 1 and 2, respectively. Walls 1 and 2 define the inner and outer bounds of an oxygenation chamber which contains a fiber bundle 3. Fiber bundle 3 comprises a plurality of hollow microporous fibers. The hollow fibers are meant to be affected externally by the blood that flows through the oxygenation chamber in the manner described hereinafter. Although the embodiments disclosed are of generally cylindrical structures and cores, it will be appreciated that the principals disclosed herein are applicable to structures and cores of other shapes such as ovals, squares, rectangles, and variations thereof. The requirement being that the structures have a core about which is positioned a fiber bundle through which blood is caused to flow in a generally circumferential path from the inlet to the outlet.

Fiber bundle 3 may be formed of semi-permeable hollow fibers according to known techniques and may have a variety of winding patterns or structures. For example, known fiber bundles and their manufacture are disclosed in the following U.S. Pat. Nos.: 5,297,591; 5,141,031; 4,172,794; 5,376,334; 3,794,468; 4,572,446; 3,422,008; 5,188,801.

These patents disclose the use of single hollow fibers, hollow fiber ribbons or hollow fiber mats to form hollow fiber bundles with various configurations and winding patterns. The hollow fiber bundles are formed about a core and have a longitudinal axis. The winding patterns can result in hollow fibers which are angled with respect to the axis of the bundle or are substantially parallel to the axis of the fiber bundle. The fiber bundle of the present invention may be formed using any of these known techniques.

The hollow fibers are embedded or sealed, at their ends, in the rings 4 and 5 of polyurethane resin, known as potting, and are connected respectively to a gas inlet chamber 6 formed in the upper lid 7 of the structure, which is provided with an inlet connector 7a, and to a gas outlet chamber 8 formed in the lower lid 9 of the structure, which is provided with an outlet connector 9a. The oxygenation chamber is thus defined by the inner and outer walls together with the rings of potting at each end of the fibers.

Oxygen, or a mixture of oxygen and nitrogen, enters the gas inlet chamber 6 through the connector 7a and enters the lumens of the hollow fibers. Differences in concentration produce a diffusive flow of oxygen toward the blood and of carbon dioxide from the blood in the opposite direction. The carbon dioxide reaches the gas outlet chamber 8 and is discharged through the connector 9a.

A significant feature of the invention resides in the presence of ribs that protrude monolithically from the inner wall 1. The ribs are divided into the three uniformly distributed sets which are generally designated by the reference numerals 10, 11 and 12 in FIG. 2 and run longitudinally along the entire axial length of the core. FIG. 1 illustrates the ribs of the set 10 designated by the reference numerals 10a–10g, and FIG. 3 illustrates the ribs of the set 11 designated by the reference numerals 11a–11g.

The shape and position of the ribs on the inner wall of the substantially cylindrical core cause the fiber bundle 3 to assume an undulated arrangement which is clearly shown in FIG. 2. This results in fiber bundle 3 touching the outer wall 2 in the regions opposite where it touches the ribs and being separated from outer wall 2 and touching the inner wall 1 in the regions that lie between two adjacent sets of ribs. The shape of the ribs will depend on the configuration and winding pattern of the hollow fiber bundle. In the embodiment disclosed a fiber bundle comprised of hollow fibers or hollow fiber ribbons wound substantially parallel to the axis of the structure or a fiber bundle comprised of one or more hollow fiber mats of any orientation would produce the undulating pattern with the rib structure disclosed. For fiber bundles comprised of hollow fibers wound at an angle with respect to the axis of the structure/core, the shape, angle and spacing of the ribs in the rib sets would be adjusted so that the desired undulating pattern is achieved.

This arrangement forms empty spaces or outer wall chambers, designated by the reference numerals 13, 14 and 15, adjacent to the outer wall 2 and a series of empty spaces or inner wall chambers adjacent to the inner wall 1 between the ribs of the three rib sets. In the drawing figures the reference numeral 16 designates, by way of example, one of the spaces that lie between the ribs of the set generally designated by the reference numeral 10.

Blood circulation is clearly indicated by the arrows shown in the drawing figures. The blood thus enters the oxygenation chamber through the blood inlet slot 17, 18 and 19 formed in the inner wall 1 in the region between the ribs 10b and 10c of the set 10. All the ribs of the set are perforated to allow the blood to distribute over the entire length of the wall, affecting the fiber bundle 3.

As best seen in FIG. 2, once the blood has entered fiber bundle 3, it splits along two identical paths which are referenced to by the arrows and flows in a circumferential path towards the empty spaces 13 and 14 and then towards the series of empty spaces that lie between the ribs of the sets 12 and 11, finally reaching the empty space 15, where it can exit through the blood outlet connector 20. For fiber bundles comprised of hollow fibers which are generally parallel to the axis of the structure the blood flow is substantially perpendicular to the fibers.

A blood circulation is thus provided which, by virtue of the presence of wide passage spaces, has very low load losses and thus allows the blood to be oxygenated with limited pressures that ensure fully negligible hemolytic damage.

The described device is completed by the connector 21 for coupling an optional recirculation circuit and by the connector 22 connected to the bubble removal chamber 23.

Figure 4:
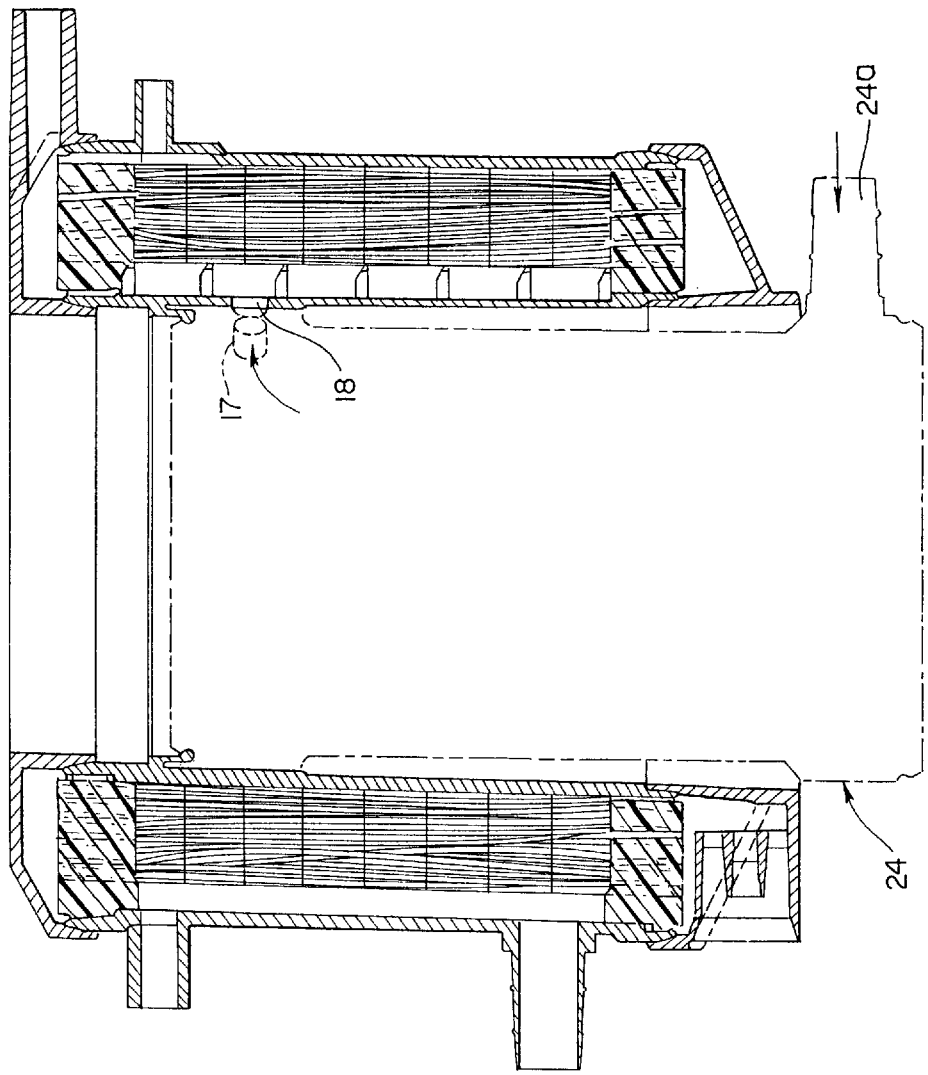
FIG. 4 is another sectional view, similar to FIG. 1, illustrating the method for inserting a heat exchanger.

FIG. 4 is a sectional view taken along the same plane as FIG. 1 and clearly illustrates the advantageous conditions allowed by the oxygenator according to the invention by means of a series coupling with a heat exchanger 24. Heat exchanger 24 can be accommodated inside the structure and conveys the blood that has entered it through the connector 24a, after adjusting its temperature, directly to the slot 17, 18 and 19 that lead into the oxygenator.

Figure 5:
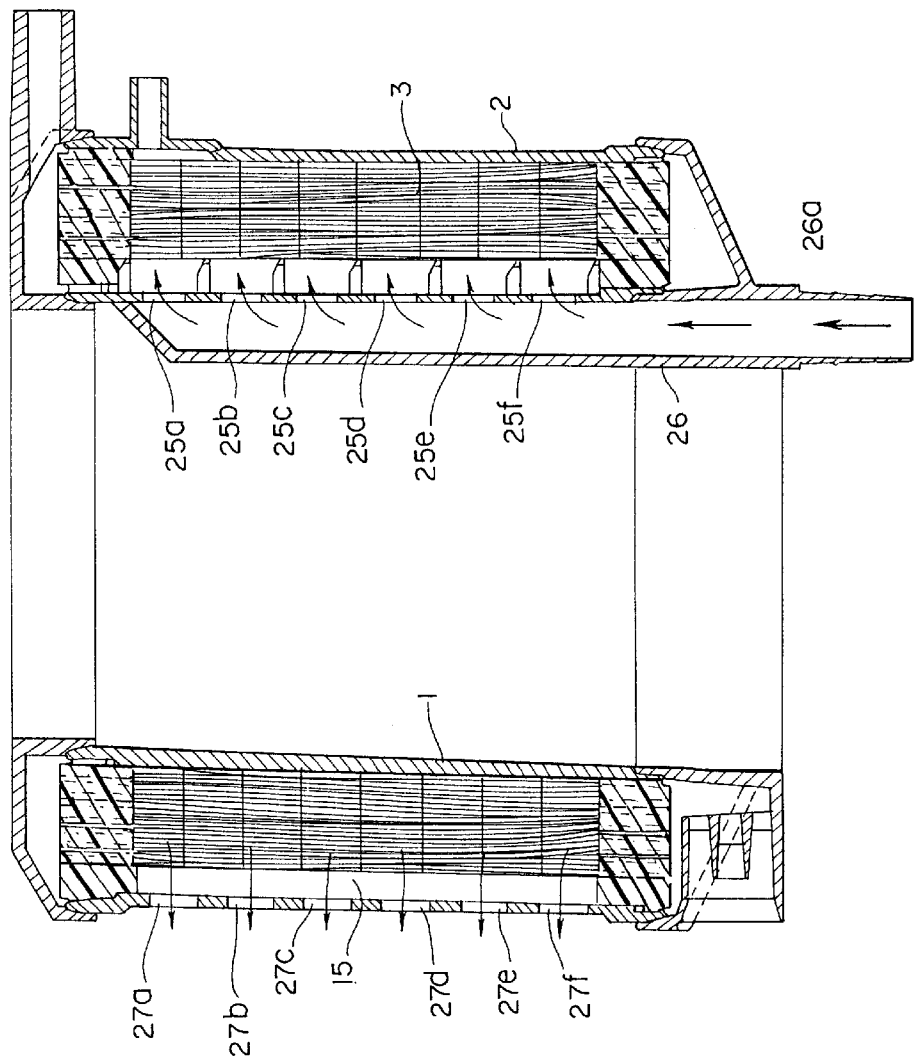
FIG. 5 is a longitudinal sectional view of the invention according to a different embodiment.

FIG. 5 illustrates a further embodiment of the invention related to the paths of blood flow into and out of the oxygenation chamber. According to this embodiment, the external connection path at the inner wall 1 is provided by means of multiple aligned slots, designated by the reference numerals 25a–25f, which are formed in the wall 1 at the regions between the ridges of the rib set 10. The slots lead into the blood inlet manifold 26 that is adjacent to the wall 1 and is provided with the blood inlet connector 26a, which can be connected to a blood supply line.

The external connection path or blood outlet at the outer wall 2 is provided, in this different embodiment, by means of the aligned slots which are designated by reference numerals 27a–27f and are formed in the wall 2 at the empty space 15 the blood that flows out of the slots can be collected by a suitable device and particularly by a heat exchanger.

FIGS. 6–9 schematically illustrate configurations according to further embodiments of the invention. These embodiments show generally that with an odd number of sets of ribs the two external connection paths of the oxygenation chamber are located, one for each wall, in diametrically opposite regions where the fiber bundle separates from the walls, i.e. in the chambers. In contrast, with an even number of sets of ribs the connection paths are both either on one wall or on the other.

In particular, FIGS. 6 and 7 relate to embodiments with three sets of ribs. FIG. 6 is a view of the solution provided in the previously described embodiment, whereas FIG. 7 illustrates the swapping of the functions of the two external connection paths, i.e., the blood outlet is now where the inlet was, and the inlet is now where the blood outlet was. The same situation for the blood inlet and outlet paths, arranged respectively on the inner wall and on the outer wall, occurs with any odd number of sets of ribs. FIGS. 8 and 9, with four sets of ribs, illustrate the arrangement of the external connection paths in the case of an even number of rib sets. Thus, with 6, 8, 10 sets and so forth, the connection paths are both located on the same wall.

FIG. 10 shows a still further embodiment of the invention. FIG. 10 is similar to FIG. 2 and illustrates a similar device except the fiber shape of the core and the fiber bundle. In FIG. 10 core 31 is not cylindrical. Rather, it has an undulating configuration with a plurality of substantially symmetrical longitudinal waves or undulations which are generally parallel with the axis of the core. A plurality of rib sets 34, 35, 36, 37 and 38 are sized and positioned to substantially fill the troughs of the waves/undulations. Thus, when fiber bundle 33 is wound over the core 31 and rib sets 34–38, it assumes a generally cylindrical shape. The structure is provided with an undulating outer wall 32 substantially symmetrical with the configuration of the core 31.

This arrangement forms empty spaces or outer wall chambers designated by the reference numerals 39, 40, 41, 42 and 43 adjacent to the outer wall 32, and a series of empty spaces or inner wall chambers adjacent to the inner wall or core 31 between the ribs of rib sets 34, 35, 36, 37 and 38. This arrangement is similar to that discussed with respect to the earlier embodiments except that the fiber bundle has a substantially cylindrical configuration instead of an undulated configuration. The construction and operation of the devices are otherwise substantially identical. Likewise, the number of undulations or chambers may be odd or even, increased or decreased, and the position of the blood inlet and outlet may be varied similar to that illustrated in FIGS. 6–9. Blood circulation is clearly indicated by the arrows shown in FIG. 10.

It has been found that the design of the present invention which includes inner wall and outer wall chambers has significantly lower pressure drop than conventional designs where the fiber bundle completely fills the oxygenation chamber between the inner and outer walls. This is supported by the following example which is a comparison test of a conventionally designed circumferential flow oxygenator without inner or outer wall chambers and a device similar to that shown in FIG. 10.

EXAMPLE

The fiber bundles of both oxygenators were constructed from Akzo two ply fiber mat having a wall thickness of 16.8 microns and an outer fiber diameter of 380 microns.

For the conventional design the total fiber length was 4.9 m, the length of the fiber bundle between potted ends was 105 mm and the effective fiber surface area was 2.06 m$^2$. For the new design the total fiber length was 5.0 m, the length of the fiber bundle between potted ends was 105 mm and the effective surface area was 2.11 m$^2$. When tested in accordance with AAMI standards with bovine blood at a flow rate of 6 l/min the conventional oxygenator had a pressure drop of 596 mmHg while the new design had a pressure drop of only 154 mmHg. At a flow rate of 8 l/min the oxygen transfer rate was 491 cc/min for the conventional design and 486 cc/min for the new design while the carbon dioxide transfer rates were 442 cc/min and 420 cc/min, respectively. As the test data indicates, the pressure drop across the fiber bundle of the present invention has been significantly reduced over that of a similarly constructed conventional device without inner and outer wall chambers. By reducing the pressure drop the device can be operated with less chance of causing hemolytic damage to the blood. This is accomplished without a meaningful loss of efficiency of oxygen and carbon dioxide transfer characteristics. Thus, the device of the present invention retains the recognized efficiency of circumferential flow oxygenators but with less chance of harming the blood.

The described invention is susceptible of numerous modifications and variations, all of which are within the scope of the inventive concept. As previously mentioned, the number and configuration of sets of ribs may be varied. Any structure or shape may be used for the core, the outer wall or the ribs sets so long as it results in the formation of a plurality of longitudinal inner and outer wall chambers. The size, number and shape of the ribs may be varied in accordance with the structure and winding pattern of the fiber bundle in order to form the inner and outer wall chambers. Thus, the rib sets may be constructed to use with a fiber bundle comprised of individual fibers, fiber ribbons, or fiber mats, wound or wrapped so that the fibers are parallel to or at an angle with respect to the axis of the core. Additionally, the configuration of the blood flow paths for connecting the oxygenation chamber to the outside can also be provided in a variety of ways.

In the practical embodiment of the invention, all the details may be replaced with other technically equivalent elements. Further, the materials employed, as well as the shapes and dimensions, may further more be varied according to the requirements.

We claim:

1. A blood oxygenator comprising:

a structure including an outer wall and a core which defines an inner wall;

a hollow fiber bundle disposed within the structure between the inner wall and the outer wall, the hollow fiber bundle comprised of hollow gas permeable fibers, each fiber having first and second ends and a hollow interior;

a first sealing element between the first ends of the hollow fibers;

a second sealing element between the second ends of the hollow fibers, the first and second sealing elements, the inner wall and the outer wall together defining an oxygenation chamber;

a blood inlet for introducing blood into the oxygenation chamber;

a blood outlet for discharging blood from the oxygenation chamber, the blood inlet and blood outlet being disposed such that blood is caused to flow circumferentially through the fiber bundle;

a gas inlet for introducing gas into the interior of the hollow fibers at the first ends of the fibers;

a gas outlet for discharging gas from the interior of the fibers at the second ends of the fibers; and a plurality of rib sets, each rib set having at least one rib extending radially from the inner wall, the rib sets running longitudinally between the inner wall and the fiber bundle, causing the fiber bundle to be spaced apart from the core to form a plurality of longitudinal inner wall chambers, such that the fiber bundle is in contact with the outer wall in regions radially opposite the inner wall chambers and such that the fiber bundle is spaced apart from the outer wall forming a plurality of outer wall chambers in regions between the rib sets where the fiber bundle is in contact with the inner wall.

2. An oxygenator according to claim 1 wherein there is an odd number of rib sets.

3. An oxygenator according to claim 2 wherein the rib sets are evenly distributed along the inner wall.

4. An oxygenator according to claim 2 wherein one of the blood inlet and the blood outlet is disposed on the core and the other is disposed on the outer wall.

5. An oxygenator according to claim 4 wherein the blood inlet and blood outlet are diametrically opposed and wherein one of the blood inlet and blood outlet is in flow communication with an inner wall chamber and the other is in flow communication with an outer wall chamber.

6. An oxygenator according to claim 1 wherein there is an even number of rib sets.

7. An oxygenator according to claim 6 wherein the rib sets are evenly distributed along the inner wall.

8. An oxygenator according to claim 6 wherein both of the blood inlet and the blood outlet are disposed along one of the core and the outer wall.

9. An oxygenator according to claim 8 wherein both the blood inlet and blood outlet are in flow communication with one of an inner wall chamber and an outer wall chamber.

10. An oxygenator according to claim 1 wherein the fiber bundle is comprised of one or more fiber mats.

11. An oxygenator according to claim 10 wherein the one or more fiber mats are comprised of hollow fibers substantially parallel to an axis of the core.

12. An oxygenator according to claim 1 wherein the hollow fibers are substantially parallel to an axis of the core.

13. An oxygenator according to claim 1 wherein the core is substantially cylindrical.

14. An oxygenator according to claim 13 wherein the rib sets protrude into the oxygenation chamber and cause the fiber bundle to assume an undulated configuration.

15. An oxygenator according to claim 1 wherein the inner wall of the core is provided with a plurality of longitudinal undulations.

16. An oxygenator according to claim 15 wherein the rib sets are positioned and configured such that the fiber bundle assumes a substantially cylindrical configuration.

17. A blood oxygenator comprising:
   a structure including an outer wall and a core which defines an inner wall;
   a hollow fiber bundle disposed within the structure between the core and the outer wall, the hollow fiber bundle comprised of hollow gas permeable fibers, each fiber having first and second ends and a hollow interior;
   means for spacing the fiber bundle from the core to form a plurality of longitudinal inner wall chambers such that the fiber bundle is in contact with the outer wall in regions radially opposite the inner wall chambers and such that the fiber bundle is spaced apart from the outer wall forming a plurality of outer wall chambers in regions between the inner wall chambers where the fiber bundle is in contact with the inner wall;
   a first sealing element between the first ends of the hollow fibers;
   a second sealing element between the second ends of the hollow fibers, the first and second sealing elements, the inner wall and the outer wall together defining an oxygenation chamber;
   a blood inlet for introducing blood into the oxygenation chamber;
   a blood outlet for discharging blood from the oxygenation chamber, the blood inlet and blood outlet being disposed such that blood is caused to flow circumferentially through the fiber bundle;
   a gas inlet for introducing gas into the interior of the hollow fibers at the first ends of the fibers; and
   a gas outlet for discharging gas from the interior of the fibers at the second ends of the fibers.

18. An oxygenator according to claim 17 wherein there is an odd number of both inner wall chambers and outer wall chambers.

19. An oxygenator according to claim 18 wherein the inner wall chambers are evenly distributed along the core.

20. An oxygenator according to claim 18 wherein one of the blood inlet and the blood outlet is disposed on the core and the other is disposed on the outer wall.

21. An oxygenator according to claim 20 wherein the blood inlet and blood outlet are diametrically opposed and wherein one of the blood inlet and blood outlet is in flow communication with an inner wall chamber and the other is in flow communication with an outer wall chamber.

22. An oxygenator according to claim 17 wherein there is an even number of both inner wall chambers and outer wall chambers.

23. An oxygenator according to claim 22 wherein the inner wall chambers are evenly distributed along the core.

24. An oxygenator according to claim 22 wherein both of the blood inlet and the blood outlet are disposed along one of the core and the outer wall.

25. An oxygenator according to claim 24 wherein both the blood inlet and blood outlet are in flow communication with one of an inner wall chamber and an outer wall chamber.

26. An oxygenator according to claim 17 wherein the fiber bundle is comprised of one or more fiber mats.

27. An oxygenator according to claim 26 wherein the one or more fiber mats are comprised of hollow fibers substantially parallel to an axis of the core.

28. An oxygenator according to claim 17 wherein the hollow fibers are substantially parallel to an axis of the core.

29. An oxygenator according to claim 17 wherein the core is substantially cylindrical.

30. An oxygenator according to claim 29 wherein the spacing means protrude into the oxygenation chamber and cause the fiber bundle to assume an undulated configuration.

31. An oxygenator according to claim 17 wherein the inner wall of the core is provided with a plurality of longitudinal undulations.

32. An oxygenator according to claim 31 wherein the spacing means is positioned such that the fiber bundle assumes a substantially cylindrical configuration.

33. A method of oxygenating blood comprising:
   providing an oxygenator having an oxygenation chamber with a blood inlet and a blood outlet, the oxygenation chamber containing a hollow fiber bundle comprised of hollow gas permeable fibers lying between an inner wall defined by a core and an outer wall, a plurality of rib sets, each rib set having at least one rib extending radially from the inner wall, the rib sets running longitudinally between the inner wall and the fiber bundle, causing the fiber bundle to be spaced apart from the core to form a plurality of longitudinal inner wall chambers, such that the fiber bundle is in contact with the outer wall in regions radially opposite the inner wall chambers and such that the fiber bundle is spaced apart from the outer wall forming a plurality of outer wall chambers in regions between the rib sets where the fiber bundle is in contact with the inner wall;
   causing oxygen to flow through the interior of the hollow fibers;
   delivering blood to the oxygenator through the blood inlet;
   causing the blood to flow circumferentially through the oxygenation chamber over the exterior of the hollow fibers; and
   discharging the blood through the blood outlet.

34. A method according to claim 33 wherein the step of providing an oxygenator includes providing an oxygenator having an odd number of both inner wall chambers and outer wall chambers.

35. A method according to claim 34 wherein the step of providing an oxygenator includes providing an oxygenator having inner wall chambers which are evenly distributed along the core.

36. A method according to claim 34 wherein the step of providing an oxygenator includes providing an oxygenator having one of the blood inlet and the blood outlet disposed on the core and the other disposed on the outer wall.

37. A method according to claim 36 wherein the step of providing an oxygenator includes providing an oxygenator having the blood inlet and blood outlet diametrically opposed and wherein one of the blood inlet and blood outlet is in flow communication with an inner wall chamber and the other is in flow communication with an outer wall chamber.

38. A method according to claim 33 wherein the step of providing an oxygenator includes providing an oxygenator having an even number of both inner wall chambers and outer wall chambers.

39. A method according to claim 38 wherein the step of providing an oxygenator includes providing an oxygenator having inner wall chambers which are evenly distributed along the core.

40. A method according to claim 38 wherein the step of providing an oxygenator includes providing an oxygenator having both the blood inlet and the blood outlet disposed along one of the core and the outer wall.

41. A method according to claim 40 wherein the step of providing an oxygenator includes providing an oxygenator having both the blood inlet and blood outlet in flow communication with one of an inner wall chamber and an outer wall chamber.

42. A method according to claim 33 wherein the step of providing an oxygenator includes providing an oxygenator having a fiber bundle which is comprised of one or more fiber mats.

43. A method according to claim 42 wherein the step of providing an oxygenator includes providing an oxygenator having one or more fiber mats which are comprised of hollow fibers substantially parallel to an axis of the core.

44. A method according to claim 33 wherein the step of providing an oxygenator includes providing an oxygenator having hollow fibers which are substantially parallel to an axis of the core.

45. A method according to claim 33 wherein the step of providing an oxygenator includes providing an oxygenator having a core which is substantially cylindrical.

46. A method according to claim 45 wherein the step of providing an oxygenator includes providing an oxygenator having spacing means which protrude into the oxygenation chamber and cause the fiber bundle to assume an undulated configuration.

47. A method according to claim 33 wherein the step of providing an oxygenator includes providing an oxygenator having an inner wall of the core which is provided with a plurality of longitudinal undulations.

48. A method according to claim 47 wherein the step of providing an oxygenator includes providing an oxygenator having spacing means which is positioned such that the fiber bundle assumes a substantially cylindrical configuration.

* * * * *